United States Patent
Fisher et al.

(10) Patent No.: US 8,680,013 B2
(45) Date of Patent: Mar. 25, 2014

(54) GROWTH INHIBITION OF COTTON WITH PENOXSULAM

(75) Inventors: Marc L. Fisher, Lantana, TX (US); Monica Sorribas Amela, Indianapolis, IN (US); Richard K. Mann, Franklin, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 240 days.

(21) Appl. No.: 13/349,622

(22) Filed: Jan. 13, 2012

(65) Prior Publication Data

US 2012/0184439 A1 Jul. 19, 2012

Related U.S. Application Data

(60) Provisional application No. 61/432,699, filed on Jan. 14, 2011.

(51) Int. Cl.
*A01N 43/90* (2006.01)

(52) U.S. Cl.
USPC .......................................................... 504/241

(58) Field of Classification Search
None
See application file for complete search history.

(56) References Cited

U.S. PATENT DOCUMENTS

| | | | |
|---|---|---|---|
| 4,755,211 A | 7/1988 | Thompson | |
| 4,849,010 A | 7/1989 | Hillemann | |
| 5,084,086 A | 1/1992 | Forney et al. | |
| 5,858,924 A | 1/1999 | Johnson et al. | |
| 2008/0234130 A1 | 9/2008 | McCutchen et al. | |
| 2010/0226951 A1 | 9/2010 | Sampson et al. | |

OTHER PUBLICATIONS

Disclosed Anonymously 462055: "2-(2,2-difluoroethoxy)-6-trifluoromethyl-N-(5,8-dimethoxy[1,2,4]triazolo[1,5-c]pyrimidin-2-yl)benzenesulfonamide and its use as a herbicide in mixtures" Research Disclosure, Oct. 2002, pp. 1832-1833.
"Penoxsulam and Its Use as a Herbicide in Mixtures for Use in Rice, Wheat, Barely, Oats, Sorghum, Corn, Maize, Ivm, Rangeland Pastures, Grasslands, Fallowland, Turf, and Aquatics" The IP.com Journal, vol. 5, No. 4, Apr. 2005, pp. 286-293.

*Primary Examiner* — Alton Pryor
(74) *Attorney, Agent, or Firm* — Robert Chang

(57) ABSTRACT

This invention concerns the use of penoxsulam as a plant growth regulator for cotton.

2 Claims, No Drawings

US 8,680,013 B2

GROWTH INHIBITION OF COTTON WITH PENOXSULAM

CROSS REFERENCE TO RELATED APPLICATIONS

This application claims the benefit of U.S. Provisional Patent Application Ser. No. 61/432,699 filed Jan. 14, 2011.

FIELD OF THE INVENTION

This invention concerns the use of penoxsulam as a plant growth regulator.

BACKGROUND OF THE INVENTION

The present invention concerns a method of controlling or inhibiting the growth of crops, particularly of cotton. Plant growth regulators are well-known for their effects on root growth, fruit set and drop, controlling or reducing plant growth and other developmental processes in crops. In cotton, plant growth regulators have the potential to promote crop earliness, control crop growth and height by reducing internode length or overall crop growth, reduce lodging, improve square and boll retention, and increase nutrient uptake. The number of plant growth regulators for cotton is limited and can require multiple applications, which increases costs and labor. In addition, the application of most of these plant growth regulators is not recommended on stressed plants. Therefore, a need for new plant growth regulators exists.

The plant growth regulating compound forming the composition of this invention is known in the art for its effect as an herbicide. Penoxsulam, 2-(2,2-difluoroethoxy)-N-(5,8-dimethoxy[1.2.4]triazolo[1,5-c]pyrimidine-2-yl)-6-(trifluoromethyl)benzenesulfonamide, is a triazolopyrimidine sulfonamide herbicide, and its herbicidal activity is described in *The Pesticide Manual*, Fifteenth Edition, 2009. Penoxsulam provides control of many broad-leaved, sedge and aquatic weeds in rice.

SUMMARY OF THE INVENTION

The present invention concerns a method of inhibiting the growth or positively impacting the health of cotton which comprises contacting the cotton plant or the locus thereof with a growth-regulating amount of penoxsulam.

DETAILED DESCRIPTION OF THE INVENTION

The term plant growth regulator is used herein to mean an active ingredient that temporarily retards, suppresses or positively impacts the growth of a plant, preferably without necrosis. A plant growth-regulating amount is an amount of active ingredient which causes the reversible plant growth regulator effect.

Plant growth regulation is exhibited by the compound of the invention when it is applied to the foliage or locus of the plant. The effect observed depends upon the cotton variety to be controlled, the application parameters of dilution, the particle size of solid components, the environmental conditions at the time of use, the specific adjuvants and carriers employed, the soil type, and the like, as well as the amount of chemical applied. These and other factors can be adjusted as is known in the art to promote a higher or lower degree of plant growth regulation. Generally, it is preferred to apply penoxsulam as a foliar, postemergence application during the vegetative or reproductive stages of the crop, to achieve the desired regulation of the growth of the plant, while maintaining the life of the plant.

The rate at which penoxsulam is applied will depend upon the particular type of cotton to be controlled, the degree of control required, and the timing and method of application. In general, the composition of the invention can be applied at an application rate from about 4 grams penoxsulam per hectare (g ai/ha) to about 70 g ai/ha, preferably from about 8.8 g ai/ha to about 70 g ai/ha.

Penoxsulam can be applied to the cotton in conjunction with one or more other herbicides to also control a wide variety of undesirable vegetation. When used in conjunction with other herbicides, penoxsulam can be formulated with the other herbicide or herbicides, tank mixed with the other herbicide or herbicides or applied sequentially with the other herbicide or herbicides. Some of the herbicides that can be employed in conjunction with penoxsulam include: bromoxynil, carfentrazone-ethyl, clethodim, clomazone, cyanazine, DCPA, dicamba, diuron, DSMA, EPTC, fluazifop, fluazifop-p, fluazifop-p-butyl, flumioxazin, fluometuron, fomesafen, glufosinate, glyphsoate, lactofen, linuron, metham, metham-sodium, metolachlor, MSMA, norflurazon, oxyfluorfen, paraquat, pendimethalin, prometryn, pyrithiobac, pyrithiobac sodium, quizalofop, S-metolachlor, sethoxydim, trifloxysulfuron, and trifluralin.

Penoxsulam can generally be employed in combination with other plant growth regulators such as mepiquat, mepiquat-chloride, giberellic acid, cytokinin, indolebutyric acid, abscisic acid and combinations thereof.

Penoxsulam can generally be employed in combination with other known herbicide safeners, such as harpin proteins, to enhance selectivity.

While it is possible to utilize penoxsulam directly as a plant growth regulator, it is preferable to use it in mixtures containing a plant growth regulating amount of the compound along with at least one agriculturally acceptable adjuvant or carrier. Suitable adjuvants or carriers should not be phytotoxic to the cotton, particularly at the concentrations employed in applying the compositions for cotton growth regulation, and should not react chemically with the compounds or other composition ingredients. Such mixtures can be designed for application directly to cotton or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank-mixed.

Suitable agricultural adjuvants useful in preparing the plant growth regulator compositions include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

In addition to the adjuvants and carriers, it is usually desirable to incorporate one or more surface-active agents into the plant growth regulating compositions containing penoxsulam. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenolalkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like.

The concentration of penoxsulam in the plant growth regulating compositions is generally from 0.001 to 98 percent by weight. Concentrations from 0.01 to 90 percent by weight are often employed. In compositions designed to be employed as concentrates, the active ingredients are generally present in a concentration from 1 to 98 weight percent, preferably 5 to 90 weight percent. Such compositions are typically diluted with an inert carrier, such as water, before application. The diluted compositions usually applied to cotton or the locus of cotton generally contain 0.0001 to 1 weight percent active ingredient and preferably contain 0.001 to 0.1 weight percent.

Such compositions containing penoxsulam can be applied to cotton or their locus by the use of conventional ground or aerial dusters, sprayers, and granule applicators, by addition to irrigation water, and by other conventional means known to those skilled in the art.

EXAMPLES

Evaluation of Postemergence Plant Growth Regulator Activity in the Greenhouse

Treatments consisted of the compounds as listed in Table 1. Formulated amounts of penoxsulam (Dow AgroSciences Granite® SC herbicide) were placed in 3-liter bottles and dissolved in a volume of 500 mL of a water solution containing Agri-dex crop oil concentrate in a 1.25% v/v ratio. Compound requirements are based upon a 0.3 L application volume at a rate of 187 liters per hectare (L/ha). Spray solutions of the mixtures were prepared by adding the stock solutions to the appropriate amount of dilution solution to form a 500 mL spray solution with active ingredients in single and two way combinations. Formulated compounds were applied to the plant material via backpack sprayer with XR 11001 nozzles calibrated to deliver 187 L/ha at a spray height of 18 inches (43 centimeters (cm)) above average plant canopy.

The treated and control plants were placed in a greenhouse in a randomized block design on greenhouse carts and watered by micro-sprinkler irrigation to prevent wash-off of the test compounds from leafy tissues. Treatments were rated at 14 to 52 days after application as compared to the untreated control plants. Visual injury ratings were scored on a scale of 0 to 10 where 0 corresponds to no injury and 10 corresponds to complete control.

Evaluation of Postemergence Plant Growth Regulator Activity in the Field

One field trial was conducted in field-grown cotton using standard herbicide small plot research methodology (Table 2). Plots were 2 rows wide by 20 ft long with 4 replicates per treatment. The cotton crop was grown using normal cultural practices for fertilization, seeding, watering, flooding and maintenance to ensure good growth of the crop and the weeds.

All treatments in the field trials were applied using a $CO_2$ backpack sprayer calibrated to apply 187 L/ha spray volume. Commercially available products of penoxsulam and mepiquat chloride were mixed in water at appropriate formulated product rates to achieve the desired rates based on a unit area of application (hectare) to achieve the desired rates as shown. Treatments were sprayed as a postemergence foliar application to cotton at 10-leaf stage application timing. Treatments were rated at 16 and 41 days after the application as compared to the untreated control plants. Visual crop injury ratings were scored on a scale of 0 to 100 where 0 corresponds to no injury and 100 corresponds to complete control. Visual weed control was scored on a scale of 0 to 100 percent where 0 corresponds to no weed control and 100 corresponds to complete control.

Tables 1 and 2 demonstrate the plant growth regulator effect of penoxsulam on cotton. All treatment results are an average of 3 to 4 replicates. Table 1 demonstrates the growth regulating activity of penoxsulam on cotton growth and increase in cotton boll production. Table 2 demonstrates the growth inhibiting activity of penoxsulam, similar to the commercial product mepiquat-chloride, while increasing the maturity of cotton bolls.

TABLE 1

Greenhouse Cotton Results

| | | | Cm Height 14DAAA | | 0-10 Scale Damage 14DAAA | | Cm Height 27DAAA | | 0-10 Scale Damage 27DAAA | | Cm Height 49DAAA | | 0-10 Scale Injury 49DAAA | | Bolls Number 52DAAA | |
|---|---|---|---|---|---|---|---|---|---|---|---|---|---|---|---|---|
| No. | Application Timing | Treatment | Rate (gr ai/ha) | | | | | | | | | | | | | |
| 1 | | Untreated | 0 | 26.7 | ab | 0 | d | 42.8 | a | 0 | f | 51.2 | a | 0 | h | 4.6 | bc |
| 2 | A | Penoxsulam | 8.8 | 17.6 | c | 4 | ab | 25.5 | e | 3.2 | bcd | 36.6 | de | 2.2 | g | 3.2 | cd |
| 3 | A | Penoxsulam | 17.5 | 15.7 | c | 4.2 | a | 21.8 | f | 3.4 | bcd | 33.5 | ef | 2.8 | f | 2.2 | de |
| 4 | A | Penoxsulam | 35 | 15.5 | c | 4.4 | a | 20.5 | fg | 3.6 | bc | 30.1 | fg | 3.6 | e | 2.8 | d |
| 5 | B | Penoxsulam | 8.8 | 28.8 | a | 0 | d | 32.7 | c | 2.8 | d | 44 | bc | 3.8 | e | 9 | a |
| 6 | B | Penoxsulam | 17.5 | 27.2 | a | 0 | d | 30.4 | cd | 3 | cd | 39.2 | cd | 4 | e | 8.4 | a |
| | LSD (P = 0.05) | | | 2.363 | | 0.62 | | 3.166 | | 0.57 | | 4.915 | | 0.46 | | 1.65 | |
| | Standard Deviation | | | 1.868 | | 0.49 | | 2.503 | | 0.45 | | 3.885 | | 0.36 | | 1.31 | |
| | CV | | | 8.88 | | 22.44 | | 9.19 | | 15.03 | | 11.14 | | 10.94 | | 34.51 | |

Means followed by same letter do not significantly differ (P = 0.05, Duncan's New MRT)
DAAA = Days After Application "A".
A = Application to 4 Leaf Cotton
B = 10 Leaf Cotton, 21 days after "A" timing
Cm = Centimeters
0-10 Scale = visual injury scale from 1 to 10, where 0 corresponds to no inury and 10 corresponds to complete control
gr ai/ha = grams of active ingredient per hectare

TABLE 2

Field Cotton Results

| | | | | | AMASS | | SOLNI | | | | | | | |
|---|---|---|---|---|---|---|---|---|---|---|---|---|---|---|
| Pest Bayer Code: | | | | | | | | | | | | | | |
| Crop: | | | Cotton | | Cotton | | | | Cotton | | Cotton | | Cotton | |
| Evaluation Unit/Scale: | | | % Visual | | % Visual | | % Visual | | % Visual | | % Visual | | % Visual | |
| Evaluation Type: | | | Injury | | Reduction | | Control | | Control | | Injury | | Reduction | | Maturity |
| Treatment-Evaluation Interval (3): | | | 16DAA | | 16DAA | | 16DAA | | 16DAA | | 41DAA | | 41DAA | | 41DAA |
| Footnote: | | | | | 1* | | | | | | | | 1* | | 2* |
| No. | Treatment | Rate (gr ai/ha) | | | | | | | | | | | | | |
| 1 | Penoxsulam | 35 | 2.5 | a | 11.3 | a | 95 | a | 88.8 | a | 3.8 | a | 10 | ab | 62.5 | a |
| 2 | Penoxsulam | 70 | 3.8 | a | 9.3 | a | 98.8 | a | 93.8 | a | 2.5 | ab | 5 | bc | 48.8 | a |
| 3 | Mepiquat-chloride | 74 | 0 | a | 11.3 | a | 95 | a | 91.3 | a | 5 | a | 13.8 | a | 53.8 | a |
| 4 | Untreated | 0 | 0 | a | 0 | b | 0 | b | 0 | b | 0 | b | 1.3 | c | 56.3 | a |
| | LSD (P = .05) | | 3.65 | | 4.73 | | 7.27 | | 6.56 | | 2.9 | | 6.63 | | 21.05 | |
| | Standard Deviation | | 2.37 | | 3.07 | | 4.72 | | 4.26 | | 1.88 | | 4.31 | | 13.66 | |
| | CV | | 158.11 | | 36.73 | | 6.13 | | 5.81 | | 62.73 | | 55.56 | | 24.84 | |

Means followed by same letter do not significantly differ (P = 0.05, Duncan's New MRT)
AMASS—*Amaranthus* spp, (pigweed)
SOLNI—*Solanum nigrum* (black nightshade)
DAA—Days after application
gr ai/ha—grams of active ingredient per hectare
1* - height reduction
2* - % open bolls

What is claimed is:

1. A method of inhibiting the growth and increasing boll production of cotton which comprises contacting a cotton plant or a locus of the cotton plant with a growth regulating amount of penoxsulam effective to inhibit growth and increase boll production.

2. The method of claim 1 in which penoxsulam is applied at a rate from about 8.8 grams penoxsulam per hectare (g ai/ha) to about 70 g ai/ha.

* * * * *